US005840711A

United States Patent [19]
Gallicchio

[11] Patent Number: 5,840,711
[45] Date of Patent: Nov. 24, 1998

[54] COMPOSITIONS CONTAINING LITHIUM INORGANIC SALTS AND ANTI-VIRAL DRUGS AND METHOD OF TREATING VIRAL INFECTIONS SUCH AS ACQUIRED IMMUNODEFICIENCY SYNDROME

[75] Inventor: Vincent S. Gallicchio, Lexington, Ky.

[73] Assignee: University of Kentucky Research Foundation, Lexington, Ky.

[21] Appl. No.: 780,913

[22] Filed: Jan. 9, 1997

Related U.S. Application Data

[63] Continuation-in-part of Ser. No. 493,479, Jun. 21, 1995, abandoned.

[51] Int. Cl.$^6$ .................................................. A61K 31/70
[52] U.S. Cl. ............................... 514/45; 514/46; 514/49; 514/50; 514/885; 514/904; 514/905; 424/677
[58] Field of Search .............................. 424/677; 514/45, 514/46, 49, 50, 885, 904, 905

[56] References Cited

U.S. PATENT DOCUMENTS

| | | |
|---|---|---|
| 2,699,418 | 1/1955 | Ter Horst . |
| 4,409,243 | 10/1983 | Lieb . |
| 4,490,385 | 12/1984 | Lieb . |
| 4,724,232 | 2/1988 | Rideout et al. ............................. 514/50 |
| 4,978,655 | 12/1990 | Lin et al. .................................... 514/50 |
| 5,026,687 | 6/1991 | Yarchoan et al. .......................... 514/50 |
| 5,116,822 | 5/1992 | DeClercq et al. .......................... 514/49 |
| 5,216,142 | 6/1993 | Horrobin et al. . |
| 5,223,271 | 6/1993 | Horrobin . |
| 5,252,333 | 10/1993 | Horrobin ................................. 514/905 |
| 5,262,174 | 11/1993 | Horrobin .................................. 514/49 |
| 5,342,951 | 8/1994 | Koszyk et al. . |
| 5,350,854 | 9/1994 | Khanna et al. . |

OTHER PUBLICATIONS

Science, vol. 260, pp. 1253–1291, 28 May 1993.
Biotechnology Business News, vol. 4, Issue 76, Mar. 25, 1994, pp. 9–10.
Gallicchio, V.S., "Lithium and the Blood." ed. V.S. Gallicchio, Lithium Therapy Monographs, Kargen, Basel, pp. 1–150, 1991.
Boggs, D.R. et al., "The hamatopoietic effects of lithium." Semin. Hematol., vol. 20, pp. 123–126, 1983.
Gallicchio, V.S., "Lithium and granulopoiesis: mechanisms of action." Lithium: Inorganic Pharmacology and Psychiatric Use. ed. N.J. Birch, IRL Press Ltd., Oxford, pp. 93–53, 1988.
Gallicchio, V.S., "Lithium stimulation of granulopoiesis: mechanism of action." Lithium and the Cell Physiology. eds. R. Bach, V.S. Gallicchio, Springer–Verlag, New York, pp. 82–93, 1990.
Gallicchio, V.S., "Effects of lithium on the hamatopoietic system." Lithium and the Blood. ed. V.S. Gallicchio, Lithium Therapy Monography, Karger, Bases, pp. 1–17, 1991.

Gallicchio, V.S. et al., "Effective modulation of the hamatopoietic toxicity associated with zidovudine exposure to murine and human hamatopoietic progenitor cells in vitro with lithium chloride." J. Int. Med., vol. 231, pp. 219–226, 1992.
Gallicchio, V.S. et al., "Modulation of the hamatopoietic toxicity associated with zidovudine in vivo with lithium carbonate." J. Int. Med., vol. 233, pp. 259–268, 1993.
Hirschman, H.S. et al., "Lithium for zidovudine induced neutropenia in AIDS." JAMA, vol. 85, p. 3588, 1988.
Roberts, D.E. et al., "Effect of lithium carbonate on zidovudine–associated neutropenia in the acquired immunodeficiency syndrome." Amer. J. Med., vol. 85, pp. 428–431, 1988.
Parenti, D.M. et al., "Effect of lithium carbonate in HIV–infected patients with immune dysfunction." J. AIDS, vol. 1, pp. 119–124, 1988.
Worthington, M. "Lack of effect of lithium carbonate on zidovudine–associated neuthropenia in patients with AIDS." J. Infect. Dis., vol. 162, pp. 777–778, 1990.
Barrios, N.J. et al., "Response to high dose steroids, immunoglubulin and lithium in HIV–1 infection and bone marrow aplasia: a case report." Lithium, vol. 3, pp. 72–74, 1992.
Gallicchio, V.S. et al., "Effect of lithium in murine immunodeficiency virus infected animals." Pathobiology, vol. 61, pp. 216–221, 1993.
Gallicchio, V.S. et al., "Effect of Lithium in Immunodeficient Animals and as Adjuvant Therapy with Zidovudine Administered to Normal Mice." Lithium in Medicine and Biology, 1993, pp. 181–197.
Gallicchio, V.S. et al., "Effect of Interleukin–1, GM–CSF, Erythropoietin, and Lithium on the Toxicity Associated with 3'–Azido–3'–Deoxythymidine (AZT) in vitro on Hematopoietic Progenitors (CFU–GM, CFU–MEG, and BFU–E) Using Murine Retrovirus–Infected Hematopoietic Cells." Journal of Leukocyte Biology, 50:580–586 (1991).
Gallicchio, V.S. et al., "Comparison of Dideoxynucleoside Drugs (ddI and Zidovudine) and Induction of Hematopoietic Toxicity Using Normal Murine Bone Marrow Cells: Effect of Lithium in vitro." Lithium, 4:189–194 (1993).
Gallicchio, V.S. et al., "Effect of lithium in immunoddeficiency: improved blood cell formation in mice with decreased hematopoiesis as the result of LP–BM5 MuLV infection." Antiviral Research, 00 (1995), in press.

*Primary Examiner*—James O. Wilson
*Attorney, Agent, or Firm*—McDermott, Will & Emery

[57] ABSTRACT

A composition and a pharmaceutical composition of lithium gamma linolenate and an anti-viral or antibiotic. A method of treating acquired immune deficiency syndrome (AIDS) with lithium gamma linolenate and zidovudine. And a method of decreasing the toxicity of an anti-viral or antibiotic including a step of administering a toxicity reducing effective amount of a composition of a lithium salt with an anti-viral or antibiotic.

6 Claims, 5 Drawing Sheets

COMPOSITIONS CONTAINING LITHIUM INORGANIC SALTS AND ANTI-VIRAL DRUGS AND METHOD OF TREATING VIRAL INFECTIONS SUCH AS ACQUIRED IMMUNODEFICIENCY SYNDROME

This application is a continuation in part of application Ser. No. 08/493,479 filed Jun. 21, 1995 now abandoned.

TECHNICAL FIELD

The present invention relates to compositions including lithium gamma-linolenate and toxic antivirals or antibiotics. Also disclosed is the use of lithium salts such as gamma-linolenate to reduce the toxicity associated with toxic antivirals or antibiotics, such as a reverse transcriptase and non-reverse transcriptase inhibitor drugs.

BACKGROUND ART

Lithium is an agent capable of influencing many aspects of blood cell production, in particular, the formation of granulocytes. Because of this property, lithium has been demonstrated to be an effective agent whenever granulocyte production is either faulty or inadequate. Several studies have demonstrated that lithium salts may possess antiviral properties against such viruses as herpes simplex virus and recently against HIV (Kinchington et al., 1993). Specifically, there have been several in vitro studies demonstrating lithium chloride, at concentrations ranging from 5 to 30 mM, inhibits herpes simplex virus replication by interfering with viral DNA synthesis (Skinner et al., 1980).

There have also been several in vitro studies involving DNA and RNA viruses demonstrating lithium chloride at concentrations ranging from 5 to 30 mM blocks herpes simplex virus (HSV) replication by interfering with viral DNA synthesis by inhibition of DNA polymerase activity for lithium carbonate.

The effective use of lithium carbonate and chloride in HIV-infected patients to ameliorate the myelosuppression associated with the clinical use of zidovudine in humans has been demonstrated (Herbert et al., 1988; Roberts et al., 1988; Amsterdam et al., 1990). One report describes lithium use in three AIDS patients where one of three responded with neutrophilia (Worthington 1990).

In one of these reports (Herbert et al., 1988), lithium was administered in order to achieve a serum lithium concentration of 0.6–1.2 mM, well within the therapeutic range observed in clinical psychiatry. Three of the 5 patients reported in this study demonstrated significant hematopoiesis and were capable of tolerating significantly higher doses of zidovudine (up to 1000 mg/day) without any observable signs of toxicity. There has been one report where lithium was administered to AIDS patients who were not receiving AZT (Parenti et al., 1988). In this study, 6 of 7 patients who received lithium for at least 4 weeks responded with neutrophilia; however, further lithium usage was limited due to the presence of lithium toxicity.

In another report (Barrios et al., 1992) a 14-year-old male patient with severe Factor VIII deficiency was found to be HIV-positive in 1985. Treatment with zidovudine was initiated in March 1989, but was discontinued after 6 months due to the development of thrombocytopenia, neutropenia, and anemia. Because myelosuppression did not improve over the following 3 months, intravenous immunoglobulin therapy was initiated. Bone marrow examination revealed severe hypoplasia with absent megakaryocytes, and erythroid and myeloid precursors. The patient was administered intravenous methylprednisolone on a 5-day treatment course along with daily oral lithium carbonate (300 mg t.i.d.). Within 3 days, "a remarkable rise" in both the absolute neutrophil and platelet counts was observed. Unfortunately, none of these clinical reports addressed the important question as to what effect, if any, did lithium have on virus production or pathogenesis.

The anti-viral drug zidovudine (AZT) has been used extensively in the treatment of acquired immune deficiency syndrome (AIDS). However, its effectiveness is limited because of the myelosuppression and bone marrow toxicity associated with its use. The inventors have previously demonstrated that lithium carbonate or lithium chloride, when combined with AZT in vitro with normal bone marrow cells or when administered in vivo to mice receiving dose-escalation AZT, reduced the myelosuppression and marrow toxicity of AZT significantly.

The monovalent cation lithium influences several functions that regulate the proliferation and differentiation of blood cells. Early undifferentiated pluripotential and committed progenitors of myeloid, erythroid and megakaryocyte lineages all respond to lithium (Gallicchio and Chen, 1980; Gallicchio et al., 1981). The subject of lithium and hematopoiesis has been reviewed previously (Gallicchio, 1991). Because of these properties, lithium has been demonstrated to induce hematopoietic recovery in animal models and in patients receiving myeloablative therapy for the treatment of malignant disease (Gallicchio, 1991). This property of lithium has also been demonstrated when combined with the anti-viral drug zidovudine (AZT) when administered in vivo (Gallicchio and Hughes, 1992) or in vivo (Gallicchio et al., 1993). Lithium not only effectively increased the number of hematopoietic progenitor cells derived from either bone marrow or spleen following administration in vivo, but also influenced the spatial location of these progenitor cells, i.e., within the endosteal marrow of bone marrow cavity (Gallicchio et al., 1994). The opoulation of cells demonstrating the greater increase following lithium administration in MAIDS mice receiving zidovudine resided in the area of the endosteal bone marrow cavity containing the undifferentiated, i.e., pluripotential progenitor cell population, indicating lithium is capable of influencing the most undifferentiated cell population within hematopoietic tissue with the greatest proliferative potential.

Testing has been performed to determine whether lithium carbonate or chloride treatment would be efficacious in ameliorating the marrow toxicity associated with the use of certain anti-viral drugs, notably zidovudine (AZT). Studies have demonstrated the effective use of lithium carbonate or chloride in reversing AZT-inducted suppression of blood cell production when combined with AZT in vitro in the presence of normal murine or human bone marrow cells or when administered to normal mice in vivo following dose-escalation of AZT.

Recent studies have suggested lithium carbonate or chloride treatment in LP-BM5 MuLV immunodeficient animals may have been associated with an inhibition in viral pathogenesis that influences the reduced immune response induced as indicated by the reduction in the splenomegaly and hypergammaglobulinemia, i.e., IgM, that is associated with MAIDS (Gallicchio et al., 1994). These results confirm the ability of lithium carbonate or chloride to influence the pathogenesis of MAIDS when administered to virus-infected animals in vivo. More recent studies have demonstrated in the MAIDS model that administration of $Li_2CO_3$ in vivo reduced the immunochematopoietic toxicity following dose-escalation of AZT (Gallicchio et al., 1995).

U.S. Pat. No. 5,223,271 to Horrobin issued Jun. 29, 1993. This patent discloses a method of treatment of a condition of the body, particularly molluscum contagiosum with lithium. Molluscum contagiosum is a common infectious skin disease caused by the chicken pox virus. Thus lithium acts as an anti-viral agent against this virus. Lithium compounds for the treatment of this viral infection include lithium succinate, lithium chloride, lithium carbonate, lithium orotate and lithium salts of polyunsaturated fatty acids. The lithium salt may be lithium gamma-linolenate or lithium dihomogamma-linolenate.

U.S. Pat. No. 2,699,418 to Horst issued Jan. 11, 1955 and discloses a process of applying lithium cyanate to mites. Lithium cyanate is used as an miticide.

U.S. Pat. No. 4,490,385 to Lieb issued Dec. 25, 1984. This patent discloses the use of lithium tranylcypromine for the treatment of inflammatory diseases. U.S. Pat. No. 4,409,243 to Lieb issued Oct. 11, 1983. The background section of this patent indicates that lithium carbonate was known in the prior art for the treatment of depression. This patent discloses a method for the treatment of auto-immune and inflammatory diseases with lithium tranylcypromine. Such auto-immune and inflammatory diseases in which excessive PGE2 synthesis have been implicated include rheumatoid and allergic arthritis; diseases induced by viruses, such as Guillain Bar syndrome, infectious mononucleosis, other viral lymphadenopathies and infections with Herpes virus; multiple sclerosis and other demyelinating diseases; hematological disorders such as hemolytic anemias and thrombocytopenias; endocrinologic disorders such as diabetes mellitus, Addison's disease, idiopathic hypoparathyroidism and chronic lymphocytic thyroiditis; collagen disorders, such as systemic lupus erythematosus; and reproductive disorders, such as infertility and eclampsia. HIV auto-immune disease is not discussed.

U.S. Pat. No. 5,252,333 to Horrobin issued Oct. 12, 1993. This patent discloses the use of lithium salts of $C_{18-22}$ polyunsaturated fatty acids as disinfecting compositions to combat transmission of viral diseases. The fatty acids include lithium gamma-linolenate and lithium dihomogamma-linolenate. The compounds are used for the treatment of Alzheimer's disease and is a biocidal agent. U.S. Pat. No. 5,216,142 to Horrobin et al. issued Jun. 1, 1993. This patent discloses the use of anti-viral agents such as AZT where a linoleyl, gamma-linolenyl or other unsaturated long chain fatty acid is born directly on a hydroxy or amino group of the sugar. The patent does not disclose or suggest a lithium salt of a linolenic acid.

European Patent No. 615752 A1 to Horrobin et al. discloses a method of treating viral infections including those of the HIV group by administering unsaturated fatty acids and their lithium salts to virally infected lymphocytes. Lithium salts of fatty acids include linoleic acid, gamolinolenic acid, dihomogamma-linolenic acid, arachidonic acid and adrenic acid.

Chemical Abstracts, Vol. 120, No. 3, abstract 23118E, discloses the use of lithium gamma-linolenate for the treatment of HIV-I infected cells. The abstract also discloses the use of anti-oxidant vitamin E to reduce the toxicity of lithium gamma-linolenate.

Chemical Abstracts, Vol. 120, No. 15, abstract 182623G to Gallicchio et al. discloses the effect of lithium in murine immuno-deficiency virus infected animals. The abstract suggests that lithium may be effective in modulating murine immuno-deficiency virus infection and may play a potential role in the patho-physiological processes associated with retroviral infection.

Chemical Abstracts, Vol. 119, No. 3, abstract 28537E discloses the preparation of cyclodextrin polysulfates for the treatment of AIDS and lithium salts thereof. Chemical Abstracts, Vol. 113, No. 11, abstract 90921E discloses methods for the synthesis of analogs of AZT.

Biotechnology Business News, Vol. 4, Issue 76, Mar. 25, 1994, pp. 9–10, discloses the development of a drug EF-13, which is made from lithium salts of polyunsaturated fatty acids and gammalinoleic acid for the treatment of HIV infection. The drug is being readied for clinical testing on AIDS patients.

Gallicchio, V. S., Hughes, N. K., Hulette, B. C. and Noblett, L. "Effect of interleukin-1, GM-CSF, erythropoietin, and lithium on the toxicity associated with 3'-azido-3'-deoxythymidine (AZT) in vitro on hematopoietic progenitors (CFU-GM, CFU-Meg, and BFU-E) using murine retrovirus-infected hematopoietic cells." *J. Leukocyte Biol.*, 50:580–586, 1981; discloses the effect of LiCl on AZT toxicity.

Gallicchio, V. S., Hughes, N. K. "Effective modulation of the haematopoietic toxicity associated with zidovudine exposure to murine and human haematopoietic progenitor stem cells in vitro with lithium chloride, *J. Leukocyte Biol.*, 50:580–586, 1981"; discloses the effect of LiCl on AZT toxicity when treating MAIDS.

Gallicchio, V. S., Hughes, N. K., Tse, K. F. "Modulation of the hematopoietic toxicity with zidovudine in vivo with lithium carbonate." *J. Intern. Med.*, 233:259–268, 1993; discloses the effect of Li2CO3 on AZT toxicity when treating MAIDS. Gallicchio, V. S., Hughes, N. K. "Comparison of dideoxynucleoside drugs (ddI and Zidovudine) and induction of hematopoietic toxicity using normal murine bone marrow cells: effect of lithium in vitro." *Lithium*, 4:189–194, 1993; discloses the effect of LiCl on AZT toxicity. *Antiviral Research*, 26:187–202.

Gallicchio, V. S., Cibull, M. L., Hughes, N. K., Tse, K. F. "Effect of lithium in murine immunodeficiency virus infected animals." *Pathobiology*, 61:216–221, 1993; discloses the effect of Li2CO3 on AZT toxicity in the treatment of MAIDS.

The composition and method of the present invention overcomes the deficiencies of prior art methods which fail to increase cell growth and reduce AZT toxicity by providing a composition comprising lithium gamma-linolenate and an anti-viral drug.

DISCLOSURE OF THE INVENTION

The present invention provides for a composition and a pharmaceutical composition comprising lithium gamma linolenate and an anti-viral or antibiotic. The pharmaceutical composition includes a cell growth increasing effective amount of lithium gamma linolenate and an anti-viral or antibiotic.

Another object of the invention is to provide a method of treating acquired immune deficiency syndrome (AIDS) comprising administering a cell growth increasing and AZT toxicity reducing effective amount of a composition comprising lithium gamma linolenate and zidovudine.

Still another object of the invention is to provide a method of decreasing the toxicity of an anti-viral or antibiotic comprising administering a toxicity reducing effective amount of a composition comprising a lithium salt with said anti-viral or antibiotic.

The above and other objects of the invention will become readily apparent to those of skill in the relevant art from the following detailed description and figures, wherein only the preferred embodiments of the invention are shown and described, simply by way of illustration of the best mode of carrying out the invention. As is readily recognized the invention is capable of modifications within the skill of the relevant art without departing from the spirit and scope of the invention.

DESCRIPTION OF THE INVENTION

Figure 1A:
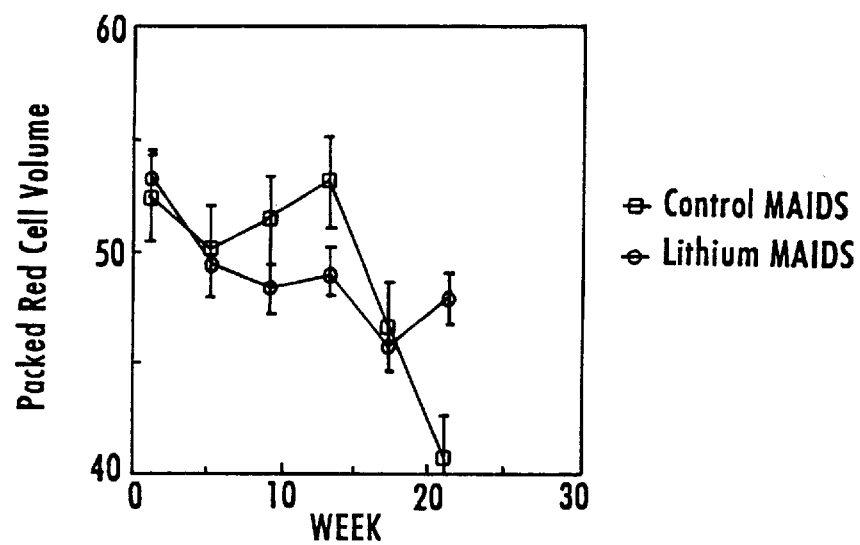
FIGS. 1(a)–1(c) show the effect of lithium on influencing peripheral blood indices from LP-BM5 MuLV-infected animals. Lithium decreased the reduction in packed red cell volume (hematocrit) (FIG. 1a), white blood cell count (FIG. 1b), and platelets (FIG. 1c) that is associated with virus infection when compared to the virus-control group not receiving lithium.

This invention concerns compositions containing lithium inorganic salts, such as lithium gamma linolenate and anti-viral drugs which would benefit from combination with lithium include the nucleoside reverse transcriptase inhibitors such as AZT, ddI, ddC, d4T; the non-nucleoside reverse transcriptase inhibitors such as neverapine; the ribonuclease reductase inhibitors such as timidox and didox; and other anti-viral compounds such as hydroxyurea, dextran sulfate and cyclophosphamide, and which are useful in treating viral infections, such as acquired immunodeficiency syndrome.

The commercial utility of the invention achieves several objectives. By combining lithium gamma linolenate with anti-viral drugs the composition: 1) improves the anti-viral efficacy of such drugs while at the same time reduce their potential to develop undesirable properties and induction of viral resistance strains; 2) provides a cost-effective drug for use in those areas of the world, e.g., under-developed and/or third world areas that are now showing the greatest increases in the number of AIDS cases, since lithium gamma linolenate is relatively inexpensive to produce; and 3) by its proven psychiatric effects, also improves and/or prevents the depression that can be associated with knowing one has a potentially fatal disease.

The invention provides a composition and a pharmaceutical composition comprising lithium gamma linolenate and an anti-viral or antibiotic. The pharmaceutical composition preferably includes a cell growth increasing effective amount of lithium gamma linolenate and an anti-viral or antibiotic. The cells which experience increased cell growth may preferably be selected from bone marrow, spleen, erythroid, myeloid and megakaryocyte cells. The anti-viral is preferably zidovudine. The anti-viral or antibiotic may preferably be selected from zidovudine, dideoxyinosine, dideocycytidine, d4T, nervapine, protease inhibitors and others listed above.

The invention also encompasses a method of treating acquired immune deficiency syndrome (AIDS) comprising administering a cell growth increasing and AZT toxicity reducing effective amount of a composition comprising lithium gamma linolenate and zidovudine (and potentially others).

In the method of decreasing the toxicity of an anti-viral or antibiotic comprising administering a toxicity reducing effective amount of a composition comprising a lithium salt with said anti-viral or antibiotic of the invention, the lithium salt may be selected from the group consisting of lithium carbonate, lithium chloride and lithium gamma linolenate. Lithium salt which is lithium gamma linolenate is preferred. The anti-viral may be selected from the group consisting of zidovudine, dideoxyinosine (ddI), dideoxycytosine (ddC), d4T, neverapine, timidox, didox, hydroxyurea, dextran sulfate and cyclophosphamide.

The examples set forth below show the unexpected cell growth and AZT toxicity reduction results obtained with lithium gamma linolenate as compared to lithium carbonate and lithium chloride. The examples further enable the making and use of the compositions of the invention.

EXAMPLE 1

When AZT is administered with a lithium salt such as lithium gamma-linolenate or lithium carbonate, a reduction in toxicity of AZT is achieved as compared to AZT where a linoleyl, gamma-linolenyl or other unsaturated long chain fatty acid is born directly on a hydroxy or amino group of the sugar.

For example, lithium gamma linolenate (LiGLA) after 4 days incubation in vitro in the presence of H9 cells that are chronically infected with HIV were 90% killed compared to only 20% for non-infected cells. Lithium gamma linolenate (LiGLA) for this study was obtained from Enfamol, Kentville, Nova Scotia, Canada.

Thus lithium gamma linolenate has been demonstrated to successfully reduce the toxicity associated with the reverse transcriptase inhibitor drug, zidovudine (AZT) following use either in vivo or in vitro. These results indicate that the clinical efficacy of lithium treatment as adjuvant therapy in AIDS patients receiving drugs like AZT improves the anti-viral action of the drug while at the same time reducing its toxicity.

Attached are two tables that identify and describe the ability of Li-GLA to influence the toxicity of AZT (Table I) and describes how these results compare with those obtained with lithium chloride. These studies were performed in vitro with normal bone marrow cells incubated in the presence of AZT and Li-GLA. This type of in vitro analysis of the ability of lithium investigated whether Li-GLA must be with lithium chloride and not lithium carbonate a lithium carbonate alters pH and therefore would interfere significantly with the culture conditions. This is a standard practice.

In summary, Table I identifies the ability of Li-GLA to influence the toxicity of AZT and in fact, increased colony formation in the presence of AZT, which was not observed when compared to lithium chloride (Table II). Use of lithium chloride reduced AZT toxicity but was not effective in increasing cell growth and colony formation. Thus, lithium gamma linolenate unexpectedly behaves differently from lithium chloride and provides an unexpected benefit of increasing healthy cell colony formation.

TABLE I

Effect of Li-GLA on AZT Bone Marrow Toxicity

| DRUG DOSE | | CFU-GM (Myeloid) | CFU-Meg (Megakaryocyte) | BFU-E (Erythroid) |
|---|---|---|---|---|
| Normal Cont | | 54.4 ± 5 (100) | 17.5 ± 3 (100) | 45 ± 4 (100) |
| Li-GLA | | | | |
| 10 µg/ml | | 66.5 ± (122)* | 32.0 ± 3 (188) | 50 ± 4 (111) |
| 15 µg/ml | | 55.5 ± (100) | 28.0 ± 4 (164) | 44 ± 4 (100) |
| 20 µg/ml | | 45.0 ± (83) | 24.0 ± 3 (141) | 31 ± 3 (68) |
| AZT | | | | |
| 0.01 µM | | 53.5 ± 3 (100)* | 16.0 ± 3 (100) | 43.5 ± 5 (100) |
| 0.1 µM | | 39.5 ± 3 (72) | 10.5 ± 3 (61) | 37.5 ± 3 (83) |
| 1.0 µM | | 28.5 ± 4 (52) | 6.5 ± 3 (38) | 21.5 ± 5 (47 |
| 10.0 µM | | 14.5 ± 3 (25) | 2.5 ± 2 (18) | 14.5 ± 2 (32) |
| AZT+ | Li-GLA | | | |
| 0.01 | 10 | 64.5 ± 3 (120)[1] | 22.5 ± 5 (140) | 41.5 ± 1 (100) |
| 0.01 | 15 | 58.5 ± 4 (107) | 21.0 ± 3 (131) | 46.5 ± 3 (106) |
| 0.01 | 20 | 57.5 ± 3 (195) | 20.5 ± 2 (120) | 49.5 ± 3 (113) |
| 0.1 | 10 | 36.5 ± 3 (100)[2] | 24.5 ± 3 (233) | 22.5 ± 3 (104) |
| 0.1 | 15 | 43.5 ± 4 (110) | 28.5 ± 2 (285) | 25.5 ± 4 (118) |
| 0.1 | 20 | 56.5 ± 3 (126) | 37.5 ± 3 (461) | 28.5 ± 2 (132) |
| 10 | 10 | 20.5 ± 3 (146)[4] | 8.0 ± 3 (320) | 18.5 ± 3 (127) |
| 10 | 15 | 22.5 ± 4 (160) | 10.5 ± 3 (420) | 21.5 ± 2 (148) |
| 10 | 20 | 26.5 ± 3 (189) | 16.5 ± 2 (660) | 25.5 ± 3 (175) |

*Compared to Normal Control
[1]Compared to 0.01 µM AZT
[2]Compared to 0.1 µM AZT
[3]Compared to 1.0 µM AZT
[4]Compared to 10.0 µM AZT

TABLE II

| | CFU-GM |
|---|---|
| AZT + LiCl | 50% |
| 0.05 mM | 42% |
| 1.0 mM | 46% |
| 3.0 mM | 47% |
| 5.0 mM | 46% |
| | CFU-Meg |
| AZT + LiCl | 50% |
| 0.05 mM | 20% |
| 1.0 mM | 165 |
| 3.0 mM | 15% |
| 5.0 mM | 25 |
| | 5 |
| | BFU-E |
| AZT + LiCl | 50% |
| 0.05 mM | 34% |
| 1.0 mM | 28% |
| 3.0 mM | 28% |
| 5.0 mM | 34% |

*Erythroid (BFU-E), myeloid (CFU-GM), and megakaryocyte (CFU-Meg).

In the presence of lithium chloride and AZT combined in vitro there is a reduction in AZT toxicity; however, the values never reach the level of the normal control. In the presence of Li-GLA not only is AZT toxicity reduced but the values are near or above those of the normal control.

Based upon these results, lithium gamma linolenate unexpectedly and advantageously improves the immune status of such patients, since it has been demonstrated lithium significantly improves immune function status, reduces the development of lymphoma that is characteristic of immunodeficiency, and increases cell growth and survival when administered in the murine model for immunodeficiency disease (MAIDS).

Additional studies from MAIDS-infected mice administered lithium salts are provided below. Treated animals demonstrated significant hematopoiesis compared to the suppressed hematopoiesis associated with LP-BM5 MuLV infection in animals not receiving lithium.

EXAMPLE 2

Mice

Female C57BL6 mice (8–10 weeks of age) were purchased from Harlan, Indianapolis, Ind., USA. All animals were quarantined for a minimum of 1-week before experimental use. Animals were housed in plastic cages and fed Purina lab chow and water ad libitum.

Infection with LP-BM5 MuLV murine immunodeficiency virus

LP-BM5 MuLV isolate used in these studies was originally derived from a bone marrow stromal cell line (SC-1) harvested from animals infected with mink cell MuLV (Morse et al., 1992) and is routinely maintained in the laboratory. LP-BM5 MuLV is a retrovirus mixture containing replication-competent helper B-trophic ecotropic mink cell focus forming (MCF) virus and an etiologic 4.9-kb replication defective genome termed EM5-def, susceptibility to which depends on the presence of the FV-1b genotype permissive for B-trophic virus replication (Morse et al., 1992). Therefore, the viral pool permissive for B-trophic virus replication (Morse et al., 1992) consisted of a mixture of B-tropic ecotropic and B-tropic mink cell focus-inducing murine immunodeficiency virus (MuLV). The titers of ecotropic and MCF MuLV were determined by XC plaque assay in SC-1 cells or by SC-1 UV-mink assay. Virus pools on average contain $10^{5.1}$–$10^{5.8}$ XC-plaque-forming units and $10^{22}$–$10^{3.2}$ focus-forming units, respectively. To minimize exogenous infection, mice were maintained in microisolator cages and handled in accordance with the NIH Guide for the Care and Use of Laboratory Animals (NIH No. 85-23, 1985). Cages, bedding and food were autoclaved prior to use and all cages and animal handling or monitoring were performed in laminar air flow hoods. Ventilation and air flow in the animal facility was set to 12 changes/h. Room temperatures were regulated at 72°±2° F. and the rooms were on automatic 12-h light/dark cycles. One hundred and twenty mice were infected by i.p. injection of 0.25 ml of LP-BM5 MuLV virus-stock (10 µg of total protein) harvested from the SC-1 cell line following 3-day in vitro culture. The development of MAIDS induced by virus was monitored by physical findings (Morse et al., 1992). Early stage MAIDS develops 5 weeks postinfection. At this time, splenomegaly could be detected by palpation. Increased systemic levels of IgM were used to monitor the development of LP-BM5 MuLV-induced disease. Death from profound immunodeficiency usually ensued within 16–24 weeks after infection.

Treatment of LP-BM5 MuLV Immunodeficient Mice (MAIDS) with Lithium

In order to evaluate the ability of lithium to influence hematopoiesis in immunodeficient virus-infected animals, the following studies were performed. One hundred and twenty mice infected with LP-BM5 were divided into two groups, i.e., 60 virus-infected mice served as virus controls and the other group was administered lithium carbonate ($Li_2CO_3$, ultra-pure; Alpha Therapeutics, Danville, Mass. USA) placed in the drinking water at a concentration of 1 mM as previously described from this laboratory (Gallicchio et al., 1993). Lithium treatment was initiated 7 days prior to virus infection. This protocol has been previously determined to provide optimum protection from LP-BM5 MuLV-induced immunodeficiency (Gallicchio and Hughes, 1993). This protocol produces an individual animal lithium dose determined to be 18 mg $Li_2CO_3$/kg/day, based upon an average daily consumption of 5.3 ml of fluid per day (Gallicchio, 1991). Lithium was initiated 7 days before virus infection and was continued for the duration of the study. Plasma lithium levels from animals bled by cardiac puncture on the days of examination were monitored by use of flame photometry (Model no. 943, IL Instruments, Lexington, Mass. USA). Virus-infected controls and virus-infected mice treated with lithium were serially sacrificed 1, 5, 9, 13, 17 and 21 weeks following virus inoculation for determination of lithium treatment on hematopoiesis following administration in LP-BMS5 MuLV infected animals.

Assessment of Hematopoiesis in LP-BM5 MuLV-Induced Immunodeficient Mice Receiving Lithium In order to evaluate the effect of lithium on hematopoiesis following administration in vivo placed in the animals' drinking water, virus-infected mice treated with or without lithium on the days of sacrifice, i.e., weeks 1, 5, 9, 13, 17, and 21 were bled (400 μl by tail bleed) prior to sacrifice for determination of peripheral blood indices, i.e., packed red cell volume (hematocrit), WBC with differential to determine absolute values for neutrophils and lymphocytes, and platelets. Bone marrow and spleen cells were assayed for their progenitor cell content, i.e., erythroid (BFU-E), myeloid (CFU-GM), and megakaryocyte (CFU-Meg) using methodology as performed routinely in the laboratory (Gallicchio et al., 1981).

Means±S.E.M. for values comparing virus control animals not receiving lithium to virus-infected animals receiving lithium from duplicate studies were determined and analyzed using the two-sample ranks test of Wilcoxan-White with a P-value<0.05 used to determine significance.

Effect of Lithium Administration on Hematopoiesis in Immunodeficient Mice

Figure 1B:
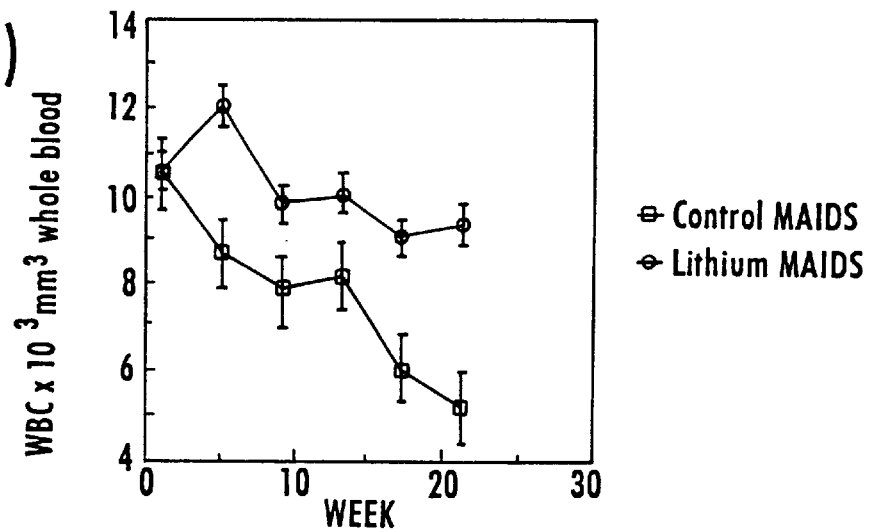
Figure 1C:
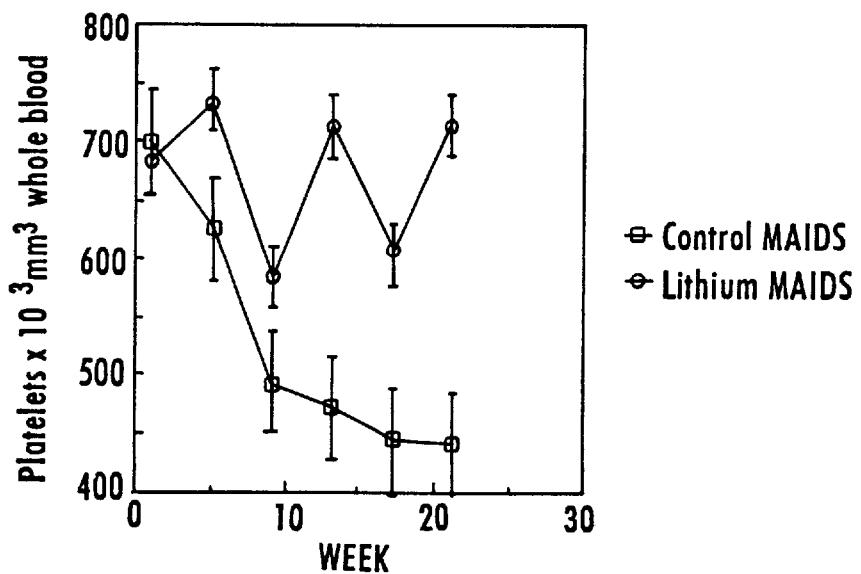
Figure 2A:
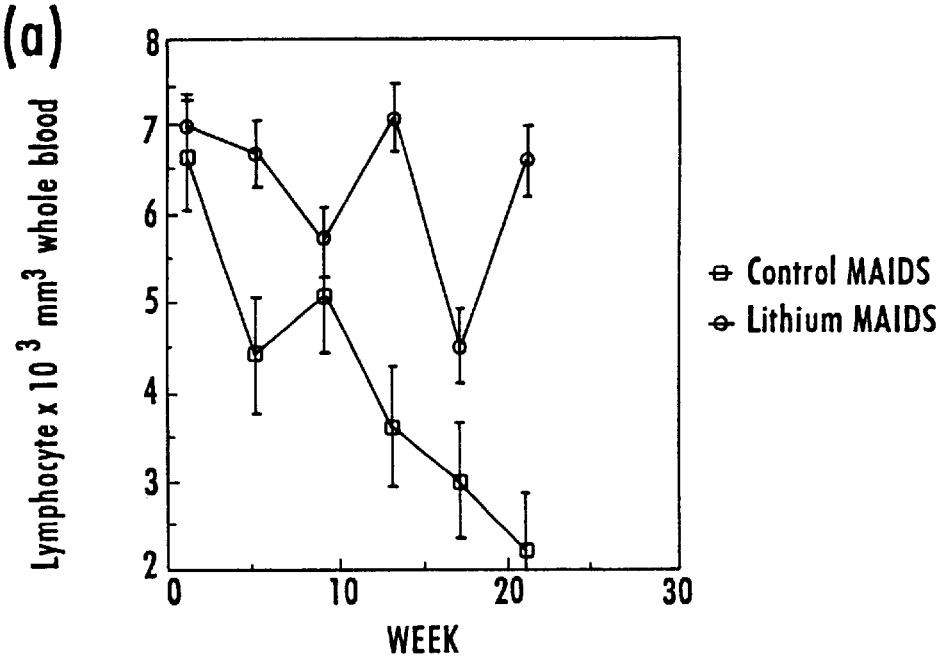
FIGS. 2(a) and 2(b) demonstrate the effect of lithium on the WBC, the differential analysis produced absolute values for neutrophils (FIG. 2a) and lymphocytes (FIG. 2b) that indicated both were increased following lithium treatment compared to the virus control group.
Figure 2B:
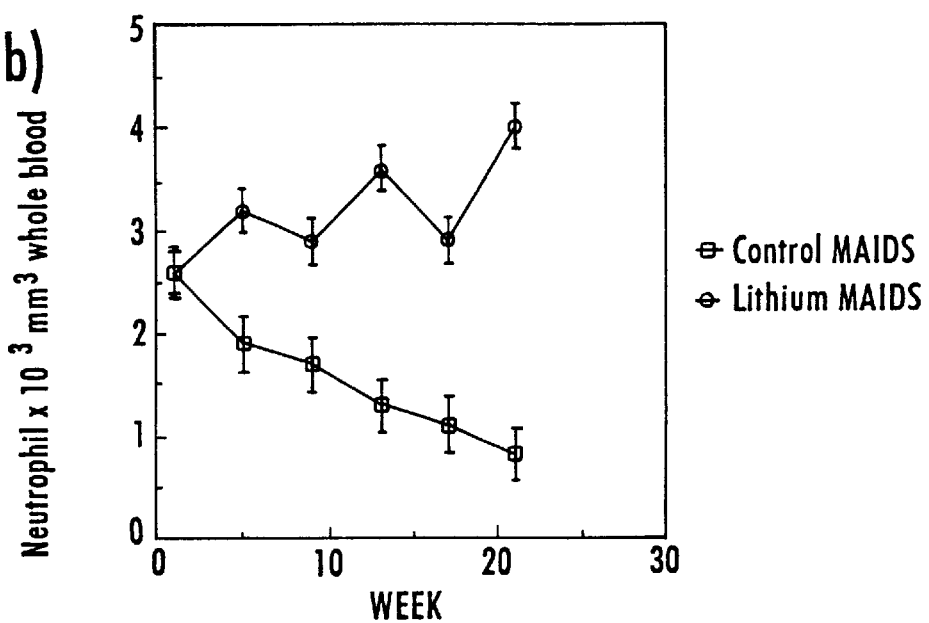

Animals inoculated with LP-BM5 MuLV developed signs of immunodeficiency disease manifested by lymphadenopathy, splenomegaly, and hypergammaglobulinemia by week 4–5 postviral infection. Disease induction and monitoring of these findings have been previously published (Gallicchio et al., 1993; Gallicchio et al., 1994). The effect of lithium on influencing peripheral blood indices from LP-BM5 MuLV-infected animals is given in FIG. 1. Lithium decreased the reduction in packed red cell volume (hematocrit) (FIG. 1a), white blood cell count (FIG. 1b), and platelets (FIG. 1c) that is associated with virus infection when compared to the virus-control group not receiving lithium. To further demonstrate the effect of lithium on the WBC, the differential analysis produced absolute values for neutrophils (FIG. 2a) and lymphocytes (FIG. 2b) that indicated both were increased following lithium treatment compared to the virus control group. Virus-infected mice receiving lithium maintained a plasma lithium concentration of 0.4–0.8 mM, well within the therapeutic range known for lithium activity in humans. There were no demonstrable signs of lithium toxicity, i.e., tremor, in any mice receiving lithium treatment during the course of study.

Figure 3A:
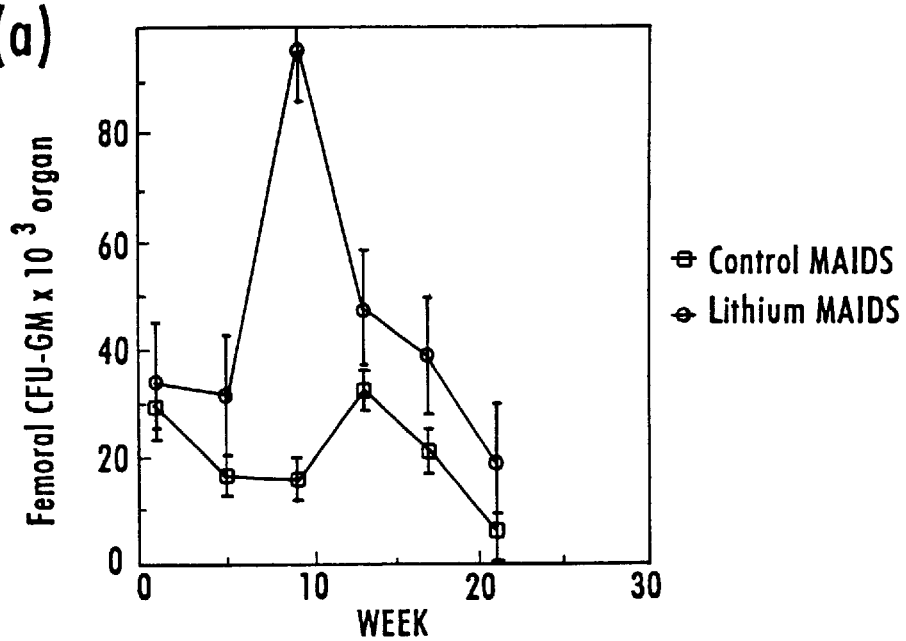
FIGS. 3(a) and 3(b) show the effect on myeloid (CFU-GM) from bone marrow and spleen is given in FIG. 3 (bone marrow (a) spleen (b)).
Figure 3B:
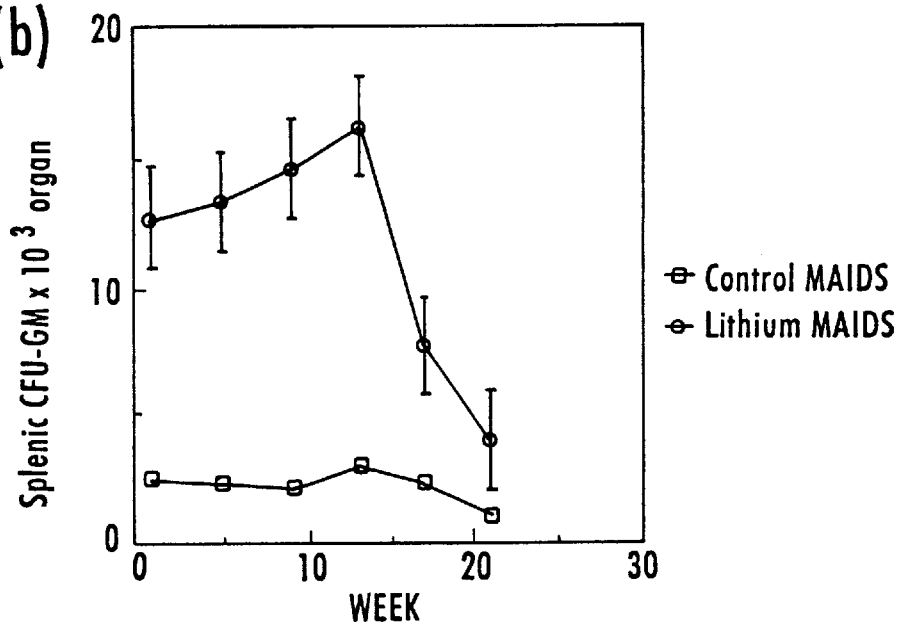
Figure 4A:
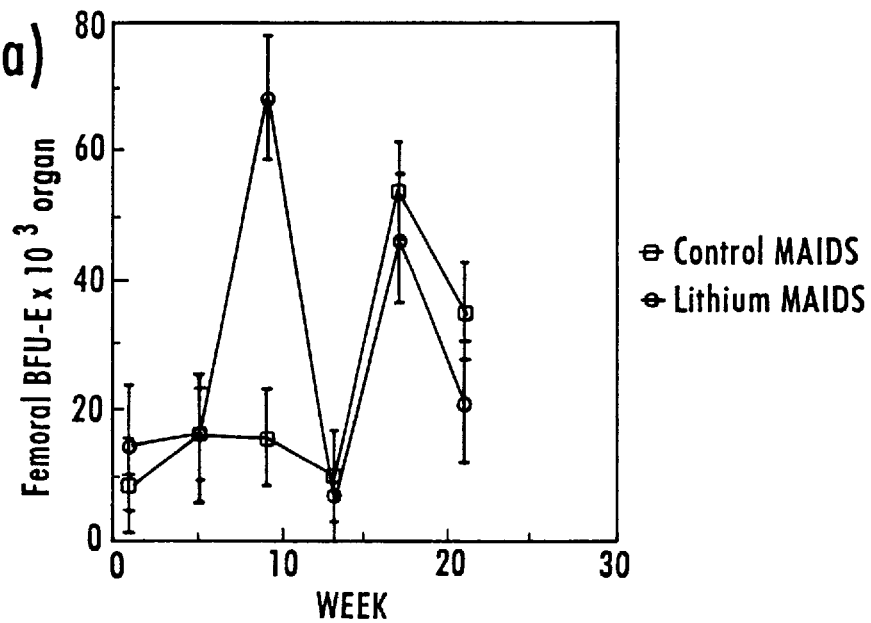
FIGS. 4(a) and 4(b) depict the effect of lithium on erythroid (BFU-E) progenitors from bone marrow (a) and spleen (b). As was observed for CFU-GM, lithium-treated virus-infected mice demonstrated increased BFU-E that peaked on week 9, all other points resembled the viral control group.
Figure 4B:
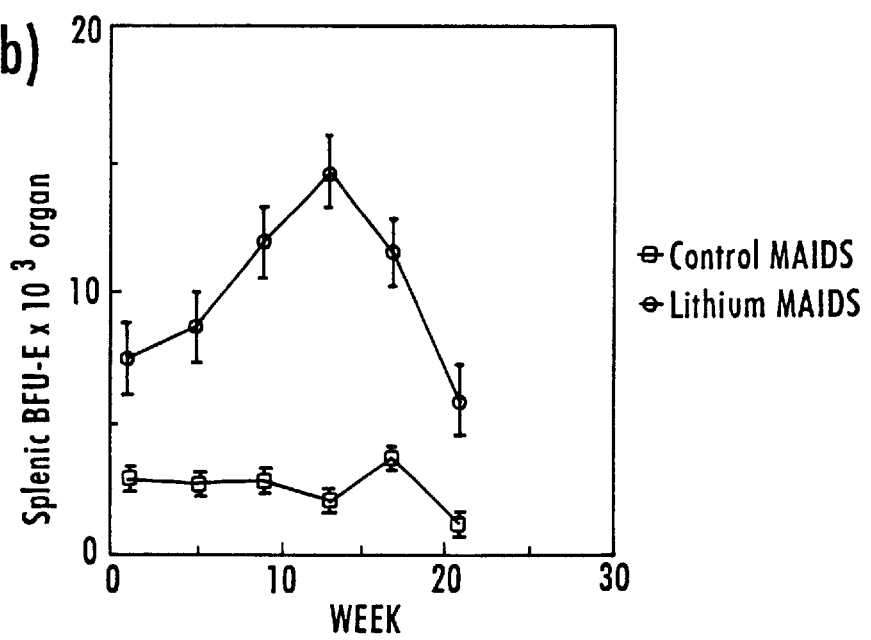
Figure 5A:
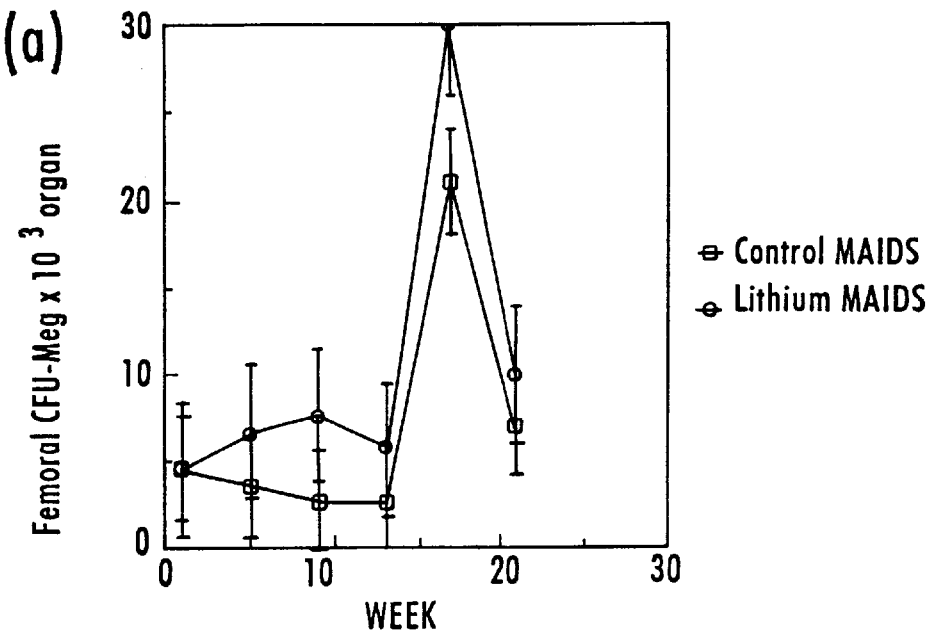
FIGS. 5(a) and 5(b) show splenic BFU-E was increased at all time points examined from the lithium-treated virus-infected group and a similar response was observed for megakaryocyte progenitors (CFU-Meg). Bone marrow CFU-Meg(a) were increased, although not until week 17 of examination, compared to week 9 for both myeloid and erythroid progenitors, while from the spleen (b), at all time points examined, CFU-Meg were increased significantly, in response to lithium treatment.
Figure 5B:
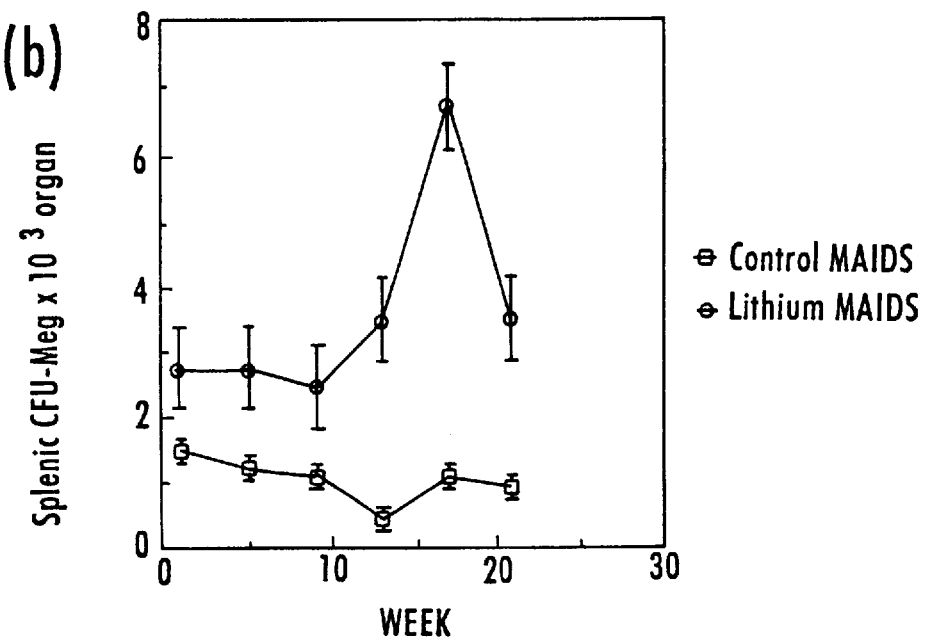

Effect of Lithium Administration on Hematopoietic Progenitor Cells in LP-BM5 MULV Immunodeficient Mice The ability of lithium to influence hematopoietic progenitor cells cultured from bone marrow and spleen comparing lithium-treated versus viral control infected mice was determined. The effect on myeloid (CFU-GM) from bone marrow and spleen is given in FIG. 3 (bone marrow (a) spleen (b)). From bone marrow, lithium increased CFU-GM compared to viral controls that peaked on week 9, otherwise the slopes of CFU-GM response were very similar. Splenic CFU-GM from lithium-treated animals was significantly increased at all time points compared to viral controls. FIG. 4 depicts the effect of lithium on erythroid (BFU-E) progenitors from bone marrow (a) and spleen (b). As was observed for CFU-GM, lithium-treated virus-infected mice demonstrated increased BFU-E that peaked on week 9, all other points resembled the viral control group. Splenic BFU-E was increased at all time points examined from the lithium-treated virus-infected group. A similar response was observed for megakaryocyte progenitors (CFU-Meg) (FIG. 5). Bone marrow CFU-Meg(a) were increased, although not until week 17 of examination, compared to week 9 for both myeloid and erythroid progenitors, while from the spleen (b), at all time points examined, CFU-Meg were increased significantly, in response to lithium treatment.

HIV-induced immunodeficiency disease has been associated with several aspects of infection which results in abnormal or insufficient hematopoiesis. Therefore, as the result of retroviral infection, pancytopenia can often develop and this condition can be exacerbated with the use of certain anti-viral drugs such as zidovudine. Although several studies have identified hematopoietic progenitor cells decrease with time as the result of retroviral infection, the precise mechanism responsible for this effect has not been clearly elucidated. In the MAIDS model, results implicated the role of the hematopoietic inductive microenvironment or stroma to be the key elements responsible for the depression of hematopoiesis associated with retroviral infection. This conclusion is based upon the observation that mice made immunodeficient as the result of LP-BM5 MuLV infection (MAIDS model), fail to establish an effective stroma capable of supporting hematopoietic progenitor cell proliferation and differentiation in vitro when evaluated in the long-term bone marrow culture system (Tse et al., 1993). Progenitor cells cultured from bone marrow harvested from LP-BM5 MuLV-infected mice responded in a normal fashion compared to marrow-derived progenitor cells from non-virus-infected control animals to the growth factors that regulate their proliferation and differentiation. Therefore, the reduced capacity to maintain normal hematopoiesis as the result of virus infection was due to an effect mediated via the microenvironment rather than to a defect in the progenitor cell population.

The inventors next evaluated the extent of lithium's capacity to modulate AZT toxicity by investigating the ability of lithium to influence blood cell production when administered to normal mice following an initial exposure to AZT. C57BL6 were administered dose-escalation AZT (1.0 mg/ml and 2.5 mg/ml) for a period of 4-weeks. This was followed by an additional 4-week period during which mice received continued AZT with the addition of lithium carbonate (1 mM). Animals were analyzed on a weekly basis for their peripheral blood indices. Animals receiving dose-escalation AZT demonstrated anemia, thrombocytopenia, and neutropenia which was dose-related. During the period when animals received combination lithium/AZT, there was significantly less anemia, thrombocytopenia, and neutropenia as compared to the AZT controls. These studies provide further evidence supporting the potential role that lithium might play in the treatment strategy of HIV-infected patients receiving anti-viral therapy.

EXAMPLE 3

C57BL6 female mice were purchased from Harlan, Indianapolis, Ind., USA used at 6–12 weeks of age, and housed 5 to a cage. To minimize exogenous infection, mice were maintained in microisolator cages and handled in accordance with the NIH Guide for the Care Use of Animals (NIH No. 85-23, 1985). Cages, bedding and food were autoclaved prior to use, and all cage changes and animal handling or monitoring was performed in laminar air flow hoods. Ventilation and air flow in the animal facility is set to 12 changes/hr. Room temperatures were regulated at 72±°F. and the rooms were on automatic 12 hr light/dark cycle. Mice received Purina Autoclavable Chow and water ad libitum until initiation of the study. Thereafter, water containing lithium was supplied to the animals and daily water consumption was monitored. To assure the microbial integrity of the study, sentinel mice were tested for possible Sendai virus using a M.A.P. test (Litton Biometrics, Charleston, S.C., USA).

Treatment of Normal Mice with Zidovudine (AZT) and Lithium

In order to evaluate the ability of lithium to influence the hematopoietic toxicity associated with AZT in mice that had already been exposed to AZT, the following protocol was established. One hundred forty-four normal mice were grouped to receive the following: (I) normal control, receiving no AZT nor lithium; (II) AZT (1.0 mg/ml) ; (III) AZT (2.5 mg/ml); (IV) lithium carbonate (1 mM); (V) AZT (1.0 mg/ml)+lithium carbonate (1 mM); and AZT (2.5 mg/ml)+ lithium carbonate (1 mM). AZT and lithium were added to the animal drinking water Groups II, III, V and VI began their AZT all at the same time. Groups V and VI, at the beginning of week 5, received lithium that was added to their water supply. All treated groups then continued to receive AZT for an additional 4 weeks, equaling a total treatment-study period lasting 8-weeks in duration. AZT in the form of the pure powder was generously supplied by Dr. P. Furman, Burroughs-Wellcome, Research Triangle Park, N.C., USA; Lithium carbonate, ultra-pure was purchased from Alpha Therapeutics, Danville, Mass., USA.

Other antivirals such as zidovudine, dideoxyinosine (ddI), dideoxycytosine (ddC), d4T, neverapine, timidox, didox, hydroxyurea, dextran sulfate and cyclophosphamide may be tested in a similar manner as set forth above.

Analysis of Hematopoietic Toxicity in Normal Mice Receiving AZT and Lithium

Animals were serially sacrificed, at least three to a group, on a weekly basis, for eight consecutive weeks. Animals were bled from the tail vein (600 µl) for assessment of peripheral blood indices; i.e., packed red cell volume, white blood cell, and platelet counts. In addition, at least one femur per animal was obtained and the bone marrow cellularity was calculated using standard laboratory procedures.

Statistical Analysis of the Data

Mean±SE for values comparing control with experimental, utilizing duplicate studies were determined and analyzed using the two-sample ranks test of Wilcoxam-White (P<0.05) to determine significance.

Effect of AZT on the Development of Hematopoietic Toxicity

Animals receiving dose-escalation AZT, i.e., 1.0 mg/ml and 2.5 mg/ml developed hematopoietic toxicity as measured by reductions in several parameters. For example, Table I shows a decrease in the hematocrit from mice receiving 1.0 mg/ml and 2.5 mg/ml. After 4-weeks of treatment, simultaneously with lithium initiation, the hematocrit levels were 82% and 62% of control, respectively, similar effects were observed for absolute neutrophils (Table III) and platelets (Table IV). After 4-weeks of AZT, mice receiving 1.0 mg/ml and 2.5 mg/ml, neutrophils were 72% and 21% of control, respectively. In regard to platelets, the results were similar with 69% and 46% after 4-weeks AZT treatment, 1.0 mg/ml and 2.5 mg/ml, respectively. An interesting finding was a reduction in the levels of absolute eosinophils. After 4-weeks treatment with AZT, the levels were 72% and 21%, respectively, corresponding to 1.0 mg/ml and 2.5 mg/ml. Lower, but less significant, levels for both lymphocytes and monocytes were also observed.

The control and 1 mg/ml AZT group animals consumed on average 5.3 ml of water per day. This corresponded to an AZT does of 240 mg/kg/day. The 2.5 mg/ml group consumed 9% less volume, which corresponded to an AZT dose of 550 mg/ml.

Effect of Lithium on the Development of the Hematopoietic Toxicity Associated With AZT Animals that received lithium following their exposure to AZT developed less toxicity as compared to animals that continued to receive AZT. For example, the hematocrit level after 8-weeks AZT (1.0 mg/ml and 2.5 mg/ml) respectively were 78% and 64% of control, compared to those animals receiving lithium and AZT (Table III). At weeks 5, 6, and 7, especially in the 2.5 mg/ml group, the toxicity measured by a reduced hematocrit was significantly different. However, at week 8, animals receiving lithium demonstrated the same level of toxicity as the AZT controls. This may indicate a tolerance to lithium developed in these animals; however, this was not observed in other parameters measured as indicated below and may reflect a more demonstrative effect on red cell production as described previously following lithium administration in vivo to normal mice.

TABLE III

Effect of Lithium on the Hematopoietic Toxicity Associated with Use of Dose-Escalation Zidovudine (AZT) Administered to Normal Mice. Values Expressed as the Percent Control Comparing the SEM from Treated versus Control Animals. Measurement of the Hematocrit. Average of at least Three-Animals per Group Analyzed per Week.
* Lithium, *P value 0.05

| Week | Normal Control | AZT 1 mg/ml | AZT 2 mg/ml | Lithium Control | Lithium + AZT 1.0 mg/ml | Lithium + AZT 2.5 mg/ml |
|---|---|---|---|---|---|---|
| 1 | 100 | 98 | 88 | 98 | 90 | 88 |
| 2 | 100 | 82 | 74 | 82 | 78 | 74 |
| 3 | 100 | 82 | 54 | 101 | 82 | 68 |
| 4 | 100 | 82 | 62 | 100 | 78 | 62 |
| 5+ | 100 | 80 | 43 | 98 | 82 | 82* |
| 6+ | 100 | 80 | 74 | 94 | 82 | 82* |
| 7+ | 100 | 78 | 58 | 98 | 78 | 74* |
| 8+ | 100 | 18 | 64 | 88 | 74 | 68 |

In observation of neutrophils, lithium produced a neutrophilia in non-AZT treated mice (Table IV). For example after 3-weeks lithium treatment, in the experimental group, neutrophils were 120% of control. In mice receiving 8-weeks AZT treatment, produced neutropenia; i.e., measured 72% and 21% of control (1.0 mg/ml and 2.5 mg/ml, respectively). In animals receiving lithium plus AZT after 4-weeks treatment, the level of neutrophils were 109% for 1.0 mg/ml and 90% for the 2.5 mg/ml treatment.

TABLE IV

Effect of Lithium on the Hematopoietic Toxicity Associated with Use of Dose-Escalation Zidovudine (AZT) Administered to Normal Mice. Values Expressed as the Percent Control Comparing the SEM from Treated versus Control Animals. Measurement of Neutrophils. Average of at least Three- Animals per Group Analyzed per Week.
* Lithium *P value 0.05

| Week | Normal Control | AZT 1 mg/ml | AZT 2 mg/ml | Lithium Control | Lithium + AZT 1.0 mg/ml | Lithium + AZT 2.5 mg/ml |
| --- | --- | --- | --- | --- | --- | --- |
| 1 | 100 | 100 | 100 | 100 | 100 | 100 |
| 2 | 100 | 58 | 36 | 54 | 43 | 87 |
| 3 | 100 | 61 | 43 | 65 | 50 | 72 |
| 4 | 100 | 72 | 21 | 61 | 47 | 65 |
| 5+ | 100 | 54 | 43 | 54 | 61* | 61* |
| 6+ | 100 | 123 | 29 | 98 | 127 | 80* |
| 7+ | 100 | 54 | 43 | 120 | 120* | 80* |
| 8+ | 100 | 72 | 54 | 90 | 109* | 90* |

In terms of platelets, lithium produced a thrombocytosis in normal mice after 3-weeks exposure that was 116% of control (Table V). After 8-weeks of AZT treatment significant thrombocytopenia was produced 83% of control for 1.0 mg/ml and 69% of control for 2.5 mg/ml. Following lithium, at each week examined for both AZT groups, there was no thrombocytopenia.

There was a significant reduction observed for eosinophils following AZT treatment (Table V). After 8-weeks treatment, the level of eosinophils was 42% of control after 1.0 mg/ml and 2% of control after 2.5 mg/ml. After initiation of lithium for 4-weeks, the level of eosinophils was 110% of control for 1.0 mg/ml 164% for 2.5 mg/ml AZT.

Based upon the volume of fluid intake, the amount of lithium consumed by animals was as follows: the lithium control (1 mM) and the 1.0 mg/ml AZT group received 18 mg lithium/kg/day, while for the 2.5 mg/ml AZT received 16 mg lithium/kg/day.

TABLE V

Effect of Lithium on the Hematopoietic Toxicity Associated with Use of Dose-Escalation Zidovudine (AZT) Administered to Normal Mice. Values Expressed as the Percent Control Comparing the SEM from Treated versus Control Animals. Measurement of Platelets. Average of at least Three- Animals per Group Analyzed per Week.
* Lithium *P value 0.05

| Week | Normal Control | AZT 1 mg/ml | AZT 2 mg/ml | Lithium Control | Lithium + AZT 1.0 mg/ml | Lithium + AZT 2.5 mg/ml |
| --- | --- | --- | --- | --- | --- | --- |
| 1 | 100 | 100 | 100 | 100 | 100 | 100 |
| 2 | 100 | 130 | 116 | 93 | 69 | 83 |
| 3 | 100 | 139 | 53 | 93 | 120 | 116 |
| 4 | 100 | 69 | 46 | 74 | 116 | 148 |
| 5+ | 100 | 69 | 83 | 69 | 176* | 176* |
| 6+ | 100 | 83 | 74 | 69 | 130* | 176* |
| 7+ | 100 | 93 | 83 | 116 | 102* | 130* |
| 8+ | 100 | 83 | 69 | 79 | 116* | |

TABLE VI

Effect of Lithium on the Hematopoietic Toxicity Associated with Use of Dose-Escalation Zidovudine (AZT) Administered to Normal Mice. Values Expressed as the Percent Control Comparing the SEM from Treated versus Control Animals. Measurement of Eosinophils. Average of at least Three- Animals per Group Analyzed per Week.
* Lithium *P value 0.05

| Week | Normal Control | AZT 1 mg/ml | AZT 2 mg/ml | Lithium Control | Lithium + AZT 1.0 mg/ml | Lithium + AZT 2.5 mg/ml |
| --- | --- | --- | --- | --- | --- | --- |
| 1 | 100 | 100 | 100 | 100 | 100 | 100 |
| 2 | 100 | 51 | 42 | 100 | 46 | 42 |
| 3 | 100 | 100 | 53 | 100 | 42 | 43 |
| 4 | 100 | 23 | 11 | 100 | 52 | 35 |
| 5+ | 100 | 46 | 23 | 100 | 100* | 100* |
| 6+ | 100 | 11 | 17 | 146 | 107* | 100* |
| 7+ | 100 | 10 | 0 | 100 | 140* | 140* |
| 8+ | 100 | 42 | 2 | 107 | 100* | 164* |

Although zidovudine (AZT) has been shown to be an effective agent in prolonging life in HIV-infected patients, it has not without two undesirable effects; i.e., the development of virus resistance and bone marrow suppression. The extent of marrow toxicity is often the dose-limiting factor in further therapy, and results in either dose-reduction or discontinuation of drug treatment.

The results of these studies indicate, as has been previously demonstrated following both in vitro and in vivo exposure in normal mice receiving AZT plus lithium marrow suppression and, therefore, hematopoietic toxicity was reduced significantly. This effect was most dramatic on circulating neutrophils, eosinophils and platelets. The effect on eosinophils is most interesting, since this is an effect that has received little attention following lithium administration. However, this context may have important implications. Immunocompromised individuals, such as those infected with HIV, characteristically become susceptible to parasitic infections that often create life-threatening situations. One of the body's natural defense mechanisms against parasitic invasion is mediated via eosinophils. The results described here demonstrate that, following AZT, the levels of these important cells are reduced significantly; thus, the capability of host-defense against these organisms may be significantly compromised following the use of such anti-viral agents as AZT. Treatment with lithium prevented this reduction in eosinophils observed with AZT. This study suggests that if lithium is administered to AIDS patients, receiving anti-viral drug therapy or not, they may be benefitted by the ability of lithium to stimulate the production of eosinophils and therefore assist in the retardation of the parasitic organisms that are characteristic of the opportunistic infections of AIDS.

The studies support the use of lithium in HIV-infected patients ameliorate the marrow suppression associated with the clinical use of AZT in humans.

In fact, there have been several reports demonstrating the effective use of lithium in HIV-infected patients in ameliorating the marrow suppression associated with the clinical use of AZT in humans; and in addition, one-report described lithium use in 5 AIDS patients, where 3 of 5 patients responded with neutrophilia. In this study, lithium was administered in order to achieve a serum concentration of 0.6–1.2 mmol, well within the therapeutic range observed in clinical psychiatry. Three of the five patients reported in this study reported significant hematopoiesis. A significant finding reported in this study was that 3 of the 5 patients receiving lithium were capable of tolerating higher doses of AZT (up to 1,000 mg). The observation period in this study did not exceed 10-weeks for one patient, with the majority of subjects being observed for only 4–5 weeks.

In a recent report, a 14-yr old male patient with severe Factor VIII-deficiency was found to be HIV positive in 1985. Treatment with AZT was initiated in March 1989, but, it was discontinued after 6-months due to the development of thrombocytopenia, neutropenia, and anemia. Because myelosuppression did not improve over the following 3 months, intravenous immunoglobulin therapy was initiated. Bone marrow examination revealed severe hypoplasia with absent megakaryocytes, red cell and white cell precursors. The patient was then given intravenous methylprednisolone on a 5-day course treatment along with daily oral lithium carbonate (300 mg tid). Within 3-days, "a remarkable rise" in both the absolute neutrophil and platelet counts were observed.

Based upon additional results reported herein, lithium gamma linolenate also significantly improves the immune status of such patients, since the use of lithium in a murine model of AIDS (MAIDS) demonstrated a significant reduction both in the degree of lymphoma and, more importantly, increased survival.

In accordance with the present invention, when the lithium salt and the antiviral or antimicrobial are administered in combination, in solution the two compounds for a single lithium salt compound. In an alternative embodiment, the compounds are preformulated as a lithium salt, as a single compound.

The present inventors have compared two anti-viral drugs, 2',2'-Dideoxyinosine (ddI) and 2,3'-Dideoxycytosine (ddC) in their triphosphate form as a lithium salt with the standard drug formulation not prepared as a lithium salt. The laboratory studies were performed in vitro to evaluate whether either drugs, i.e., with or without their lithium formulation when combined with either normal bone marrow cells or bone marrow cells taken from MAIDS animals would express: 1) differences in their toxicity profile when measured in culture and 2) differences comparing the responses using normal bone marrow cells versus bone marrow cells from MAIDS animals, in other words, comparing viral-infected cells with non-viral infected cells.

The results of these studies as described in the following Table VII:

TABLE

Comparison Between Triphosphate Forms of ddC and ddI versus Triphosphate Forms of ddC and ddI Prepared as a Lithium Salt on Bone Marrow Progenitors either Myeloid (CFU-GM) and Erythroid (BFU-E) for $ID_{50}$ Values Using Normal and Retrovirus Infected Bone Marrow Cells.

|  | CFU-GM | BFU-E |
|---|---|---|
| | Normal Bone Marrow | |
| ddI | 100 $\mu$M | 1 $\mu$M |
| ddI/Li | 250 $\mu$M | 200 $\mu$M |
| ddC | 10 $\mu$M | 0.6 $\mu$M |
| ddC/Li | 275 $\mu$M | 100 $\mu$M |
| | Virus Infected Bone Marrow | |
| ddI | 100 $\mu$M | 1 $\mu$M |
| ddI/Li | 50 $\mu$M | 0.1 $\mu$M |
| ddC | 10 $\mu$M | 10 $\mu$M |
| ddC/Li | 5 $\mu$M | 5 $\mu$M |

This table is interpreted as follows. In the presence of the $ID_{50}$ dose, i.e., the concentration of the drug at which 50% of the target cells in question were eliminated, the drug, whether ddI or ddC, when formulated as a lithium salt, the $ID_{50}$ concentration was increased. This means that more drug, when formulated as a lithium salt, was required to inhibit 50% of the target population than when the drug was analyzed not in its lithium formulation. The differences were highly significant and were observed for the two types of cells analyzed, i.e., CFU-GM and BFU-E. The second and no less important interpretation of the data demonstrates that less drug in the lithium formulation is required to inhibit 50% of the target cells than the non lithium formulated drug was analyzed when viral-infected bone marrow cells were used in the test analysis. These results are interpreted and indicate that the drug in its lithium formulation unexpectedly exhibited an enhanced anti-viral effect.

In one embodiment, the present invention shows that the addition of lithium directly to gamma linolenate improves the anti-viral efficacy of the drug while at the same time reduces the drugs potential to induce toxicity as well as improve the solubility of the compound.

The present invention, in a preferred embodiment, encompasses one drug, formulated as a lithium salt that would be administered not in combination, since the formulation is created as a single drug.

Pharmaceutical Composition Example

For the purpose of this invention, the racemic mixtures of the lithium salts and the dextro and levo forms are included within the present invention. The racemic mixtures and the dextro forms are preferred.

Further, the compounds of the present invention are useful in pharmaceutical compositions for systemic administration to humans and animals in unit dosage forms, such as tablets, capsules, pills, powders, granules, suppositories, sterile parenteral solutions or suspensions, sterile non-parenteral solutions or suspensions oral solutions or suspensions, oil in water or water in oil emulsions and the like, containing suitable quantities of an active ingredient. Topical application can be in the form of ointments, creams, lotions, jellies, sprays, douches, and the like. For oral administration either solid or fluid unit dosage forms can be prepared with the compounds of the invention. The compounds are useful in pharmaceutical compositions (wt %) of the active ingredient with a carrier or vehicle in the composition in about 1 to 20% and preferably about 5 to 15%.

Either fluid or solid unit dosage forms can be readily prepared for oral administration. For example, the compounds of the invention can be mixed with conventional ingredients such as dicalciumphosphate, magnesium aluminum silicate, magnesium stearate, calcium sulfate, starch, talc, lactose, acacia, methyl cellulose and functionally similar materials as pharmaceutical excipients or carriers. A sustained release formulation may optionally be used. Capsules may be formulated by mixing the compound with a pharmaceutical diluent which is inert and inserting this mixture into a hard gelatin capsule having the appropriate size. If soft capsules are desired a slurry of the compound with an acceptable vegetable, light petroleum, or other inert oil can be encapsulated by machine into a gelatin capsule.

Suspensions, syrups and elixirs may be used for oral administration of fluid unit dosage forms. A fluid preparation including oil may be used for oil soluble forms. A vegetable oil such as corn oil, peanut oil or safflower oil, for example, together with flavoring agents, sweeteners and any preservatives produces an acceptable fluid preparation. A surfactant may be added to water to form a syrup for fluid unit dosages. Hydro-alcoholic pharmaceutical preparations may be used having an acceptable sweetener such as sugar, saccharine or a biological sweetener and a flavoring agent in the form of an elixir.

Pharmaceutical compositions for parenteral and suppository administration can also be obtained using techniques standard in the art. The above and other compositions can be present in the reservoir alone or in combination form with pharmaceutical carriers. The pharmaceutical carriers acceptable for the purpose of this invention are the art known carriers that do not adversely affect the drug, the host, or the material comprising the drug delivery device. Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrolidone); and the like, alone, or with suitable dispensing agents such as lecithin; polyoxyethylene stearate; and the like. The carrier may also contain adjuvants such as preserving stabilizing, wetting, emulsifying agents and the like together with the penetration enhancer of this invention.

The effective dosage for mammals may vary due to such factors as age, weight activity level or condition of the subject being treated. Typically, an effective dosage of a compound according to the present invention is about 300 mg/kg/bw when administered by either oral or rectal dose from 1 to 3 times daily. A plasma lithium concentration of 0.4–0.8 mM, well within the therapeutic range known for lithium activity in humans, is preferred. The required dose is when administered parenterally, preferably about 300 mg/kg/bw may be administered intramuscularly or transdermally, 1 or 2 times a day for an adult human.

REFERENCES

1. Gallicchio V S (1991) *Lithium and the Blood.* ed; V S Gallicchio, Lithium Therapy Monographs, Karger, Basel, pp. 1–150.

2. Boggs D R and Joyce R A (1983) The hematopoietic effects of lithium. Semin Hematol 20:123–126.

3. Gallicchio V S (1988) Lithium and granulopoiesis: mechanisms of action. In; *Lithium: Inorganic Pharmacology and Psychiatric Use.* ed; N J Birch, IRL Press Ltd., Oxford, pp. 93–53.

4. Gallicchio V S (1990) Lithium stimulation of granulopoiesis: mechanism of action In; *Lithium and the Cell Physiology,* eds; R Bach, V S Gallicchio, Springer-Verlag, New York, 82–93.

5. Gallicchio V S (1991) Effects of lithium on the hematopoietic system. In; *Lithium and the Blood.* ed; V S Gallicchio, Lithium Therapy Monographs, Karger, Basel, pp. 1–17.

6. Gallicchio V S, Hughes N K (1992) Effective modulation of the hematopoietic toxicity with zidovudine exposure to murine and human hematopoietic progenitor cells in vitro with lithium chloride. *J Int Med* 23:219–226.

7. Gallicchio V S, Hughes N K, Tse K F (1993) Modulation of the hematopoietic toxicity associated with zidovudine in vivo with lithium carbonate. *J Int Med* 233:259–268.

8. Herbert Hirschman S, Jacobsen J. (1988) Lithium for zidovudine induced neutropenia in AIDS. *JAMA* 85:3588.

9. Roberts D E, Berman S M, Nakasato S, Wyle F A, Wishman R M, Segal G P. (1988) Effect of lithium carbonate on zidovudine-associated neutropenia in the acquired immunodeficiency syndrome. *Amer J Med* 85:428–431.

10. Parenti D M, Semin G L, Scheib R G. (1988) Effect of lithium carbonate in HIV-infected patients with immune dysfunction. *J AIDS* 1:119–124.

11. Worthington M. (1990) Lack of effect of lithium carbonate on zidovudine-associated neutropenia in patients with AIDS. *J Infect Dise* 162:777–778.

12. Barrios N J, Betancourt D, Paulus A, Kirkpatrick D V. (1992) Response to high dose steroids, immunoglobulin and lithium in HIV-1 infection and bone marrow aplasia: a case report. *Lithium* 3:72–74.

13. Gallicchio V S, Cibull M L, Hughes N K, Tse K F. (1993) Effect of lithium in murine immunodeficiency virus infected animals. *Pathobiology* 61:216–221.

The purpose of the above description and examples is to illustrate some embodiments of the present invention without implying any limitation. It will be apparent to those of skill in the art that various modifications and variations may be made to the composition and method of the present invention without departing from the spirit or scope of the invention. All patents and publications cited herein are incorporated by reference in their entireties.

I claim:

1. A composition comprising a lithium gamma linolenate salt of an anti-viral selected from the group consisting of AZT, dideoxyinosine (ddI), dideoxycytosine (ddC), and d4T, and an excipient.

2. A composition as in claim 1, wherein said anti-viral is AZT.

3. A method of decreasing the toxicity of an anti-viral in a human comprising administering a toxicity reducing effective amount of a lithium salt of an anti-viral selected from the group consisting of AZT, dideoxyinosine (ddI), dideoxycytosine (ddC), and d4T, wherein said lithium salt is selected from the group consisting of lithium carbonate, lithium chloride, lithium sulfate, lithium citrate and lithium gamma linolenate.

4. A method as in claim 3, wherein said lithium salt is lithium gamma linolenate.

5. A method of decreasing the toxicity of an anti-viral as in claim 3, wherein said toxicity reducing effective amount is a plasma lithium concentration of 0.4–0.8 mM.

6. A method of decreasing the toxicity of an anti-viral as in claim 3, wherein said toxicity reducing effective amount is about 300 mg/kg per body weight.

* * * * *

UNITED STATES PATENT AND TRADEMARK OFFICE
CERTIFICATE OF CORRECTION

PATENT NO. : 5,840,711
DATED : November 24, 1998
INVENTOR(S) : Vincent S. GALLICCHIO It is certified that error appears in the above-identified patent and that said Letters Patent is hereby corrected as shown below:

Title page, item [54] and
  Column 1, line 3,   in the Title change "METHOD" to
--METHODS--

Signed and Sealed this

Thirtieth Day of March, 1999

Attest:

Attesting Officer

Q. TODD DICKINSON
Acting Commissioner of Patents and Trademarks